United States Patent
Jurich et al.

(10) Patent No.: US 11,779,208 B2
(45) Date of Patent: Oct. 10, 2023

(54) TRACKING MOVEMENT OF AN EYE WITHIN A TRACKING RANGE

(71) Applicant: Alcon Inc., Fribourg (CH)

(72) Inventors: Jessica Jurich, Berlin (DE); Horia Grecu, Berlin (DE); Martin Gründig, Rangsdorf (DE); Tobias Jura Rapoport, Berlin (DE)

(73) Assignee: Alcon Inc., Fribourg (CH)

( * ) Notice: Subject to any disclaimer, the term of this patent is extended or adjusted under 35 U.S.C. 154(b) by 0 days.

(21) Appl. No.: 17/675,383

(22) Filed: Feb. 18, 2022

(65) Prior Publication Data

US 2022/0167844 A1    Jun. 2, 2022

Related U.S. Application Data

(63) Continuation of application No. 16/139,151, filed on Sep. 24, 2018, now Pat. No. 11,284,794.

(60) Provisional application No. 62/568,969, filed on Oct. 6, 2017.

(51) Int. Cl.
    *A61B 3/113*    (2006.01)
    *A61B 3/00*    (2006.01)
    *A61F 9/008*    (2006.01)

(52) U.S. Cl.
    CPC .......... *A61B 3/113* (2013.01); *A61B 3/0025* (2013.01); *A61F 9/008* (2013.01); *A61F 2009/00846* (2013.01); *A61F 2009/00897* (2013.01)

(58) Field of Classification Search
    CPC ........ A61B 3/113; A61B 3/0025; A61F 9/008
    USPC .................................................. 351/205, 209
    See application file for complete search history.

(56) References Cited

U.S. PATENT DOCUMENTS

| | | | | |
|---|---|---|---|---|
| 6,280,436 | B1* | 8/2001 | Freeman | A61F 9/008 606/4 |
| 8,591,030 | B2* | 11/2013 | Grecu | G06V 40/18 351/209 |
| 9,516,996 | B2* | 12/2016 | Diolaiti | A61B 1/00009 |
| 9,550,029 | B2* | 1/2017 | Boyden | A61B 90/11 |
| 2013/0038835 | A1 | 2/2013 | Kitajima et al. | |
| 2015/0338915 | A1* | 11/2015 | Publicover | H04N 23/90 345/633 |
| 2016/0191887 | A1* | 6/2016 | Casas | A61B 34/10 348/47 |

FOREIGN PATENT DOCUMENTS

JP    2013039148 A    2/2013

* cited by examiner

*Primary Examiner* — James R Greece

(57) ABSTRACT

In certain embodiments, a system for tracking movement of an eye comprises a camera system, a computer system, and an output device. The camera system generates images of the eye. The computer system stores the images and at least one of the images as a reference image. The computer system also tracks movement of the eye within a tracking range by comparing a current image with the reference image, and by determining a movement of the eye from the comparison of the current image and the reference image. The tracking range has one or more alert points. The computer system also determines an orientation of the eye relative to at least one alert point of the tracking range. The output device outputs a range indicator that indicates the orientation of the eye relative to the at least one alert point of the tracking range.

19 Claims, 5 Drawing Sheets

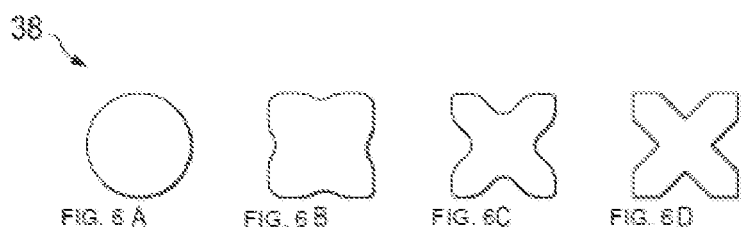
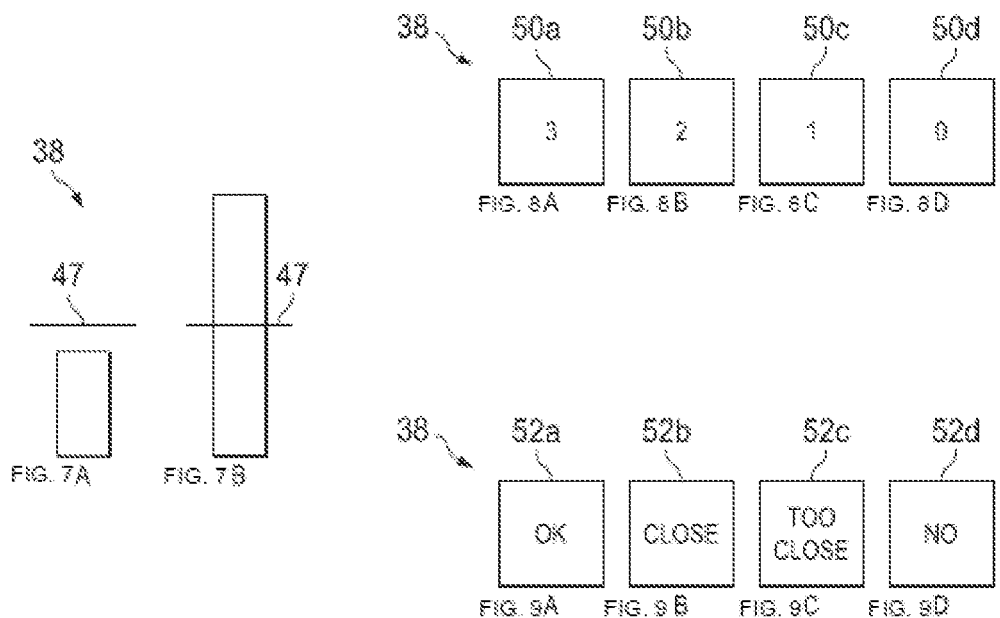

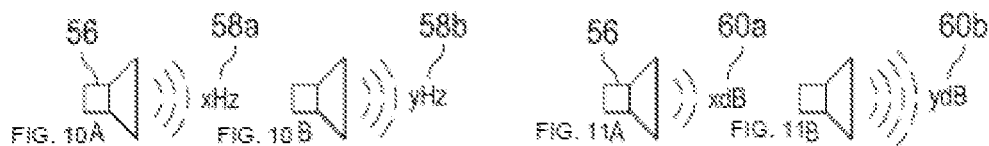
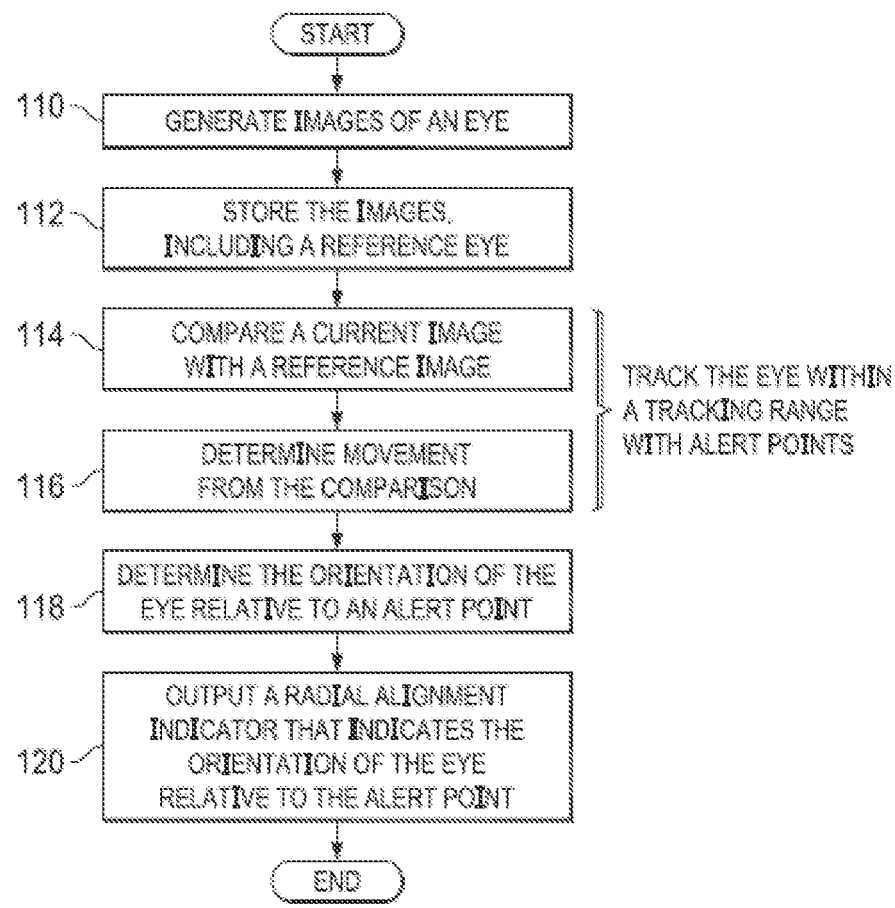
FIG. 12

TRACKING MOVEMENT OF AN EYE WITHIN A TRACKING RANGE

TECHNICAL FIELD

The present disclosure relates generally to eye-tracking, and more specifically to tracking movement of an eye within a tracking range.

BACKGROUND

Image guided systems have been developed for use with ophthalmic surgical devices, such as cataract refractive and LASIK surgical devices. The systems create a digital image of the patient's eye that capture features of the eye, e.g., scleral vessels, limbus, and iris features. This image is used to, e.g., position incisions and lens alignment in real time. The systems may have eye-tracking capabilities that detect translational and rotational movement of the eye. In some systems, eye-tracking helps keep the laser beam on target during surgery. Studies have shown that eye-tracking produces better outcomes and decreases complications.

BRIEF SUMMARY

In certain embodiments, a system for tracking movement of an eye comprises a camera system, a computer system, and an output device. The camera system generates images of the eye. The computer system comprises a memory and one or more processors. The memory stores the images and at least one of the images as a reference image. The processors track movement of the eye within a tracking range by comparing a current image of the plurality of images with the reference image, and by determining a movement of the eye from the comparison of the current image and the reference image. The tracking range has one or more alert points. The processors also determine an orientation of the eye relative to at least one alert point of the tracking range. The output device outputs a range indicator that indicates the orientation of the eye relative to the at least one alert point of the tracking range.

In certain embodiments, a method for tracking the movement of an eye comprises generating images of the eye. The images are stored and at least one of the images is stored as a reference image. Movement of the eye is tracked within a tracking range by comparing a current image of the plurality of images with the reference image, and by determining a movement of the eye from the comparison of the current image and the reference image. The tracking range has one or more alert points. An orientation of the eye is determined relative to at least one alert point of the tracking range. A range indicator that indicates the orientation of the eye relative to the at least one alert point of the tracking range is output.

BRIEF DESCRIPTION OF THE DRAWINGS

Embodiments of the present disclosure are described by way of example in greater detail with reference to the attached figures, in which:

FIGS. 5A to 5D illustrate an example of a graphical element that changes color;

FIGS. 6A to 6D illustrate an example of a graphical element that changes shape;

FIGS. 7A and 7B illustrate an example of a graphical element that changes size;

FIGS. 8A to 8D illustrate an example of a graphical element that displays numbers;

FIGS. 9A to 9D illustrate an example of a graphical element that displays words;

FIGS. 10A and 10B illustrate an example of a sound that changes in frequency;

FIGS. 11A and 11B illustrate an example of a sound that changes in volume; and

FIG. 12 illustrates an example of a method for tracking the movement of an eye that may be performed by system of FIG. 1.

DESCRIPTION OF EXAMPLE EMBODIMENTS

Referring now to the description and drawings, example embodiments of the disclosed apparatuses, systems, and methods are shown in detail. As apparent to a person of ordinary skill in the field, the disclosed embodiments are exemplary and not exhaustive of all possible embodiments.

Figure 1:
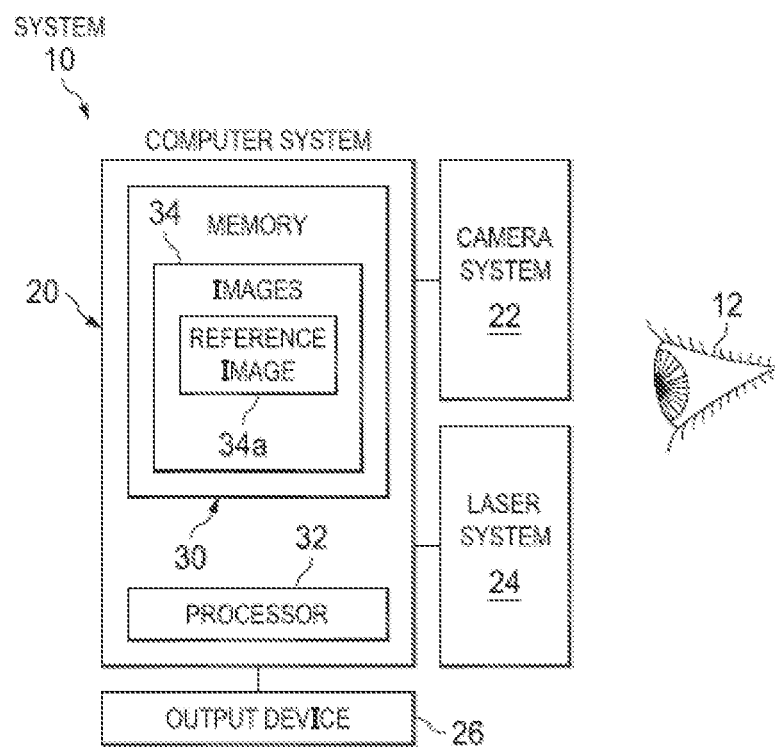
FIG. 1 illustrates one embodiment of a system for tracking the movement of an eye during laser treatment surgery.

FIG. 1 illustrates one embodiment of a system 10 for tracking the movement of an eye 12, e.g., during a surgical or diagnostic procedure. System 10 provides a range indicator that indicates the orientation of eye 12 relative to an alert point of the eye tracking range, so a user can determine if eye 12 is close to moving outside of the tracking range before it actually does. This can be used to avoid some undesirable effects of moving outside of the tracking range. For example, in some systems, if the tracking range is exceeded, the system suspends tracking, which prolongs surgery time. As another example, the system may report false positive tracking if the tracking range is exceeded.

In the illustrated embodiment, system 10 comprises a computer system 20, a camera system 22, a laser system 24, and an output device 26. Computer system 20 includes one or more memories 30 and one or more processors 32. In certain embodiments, camera system 22 generates images 34 of eye 12. Computer system 20 controls eye tracking and laser control. Memory 30 stores images 34, where at least one image 34 is stored as a reference image 34a. Processor 32 tracks eye 12 within a tracking range by comparing a current image 34 with reference image 34a and determining movement of eye 12 (e.g., change in location and/or angular orientation) from the comparison of current image 34 and reference image 34a. The tracking range has one or more alert points near or at the end of the tracking range of system 10. Processor 32 determines the orientation of eye 12 relative to an alert point. Output device 26 outputs a range indicator that indicates the orientation of eye 12 relative to the alert point of the tracking range.

Camera system 22 may be any suitable system with detectors that can detect light reflected from eye 12 and generate a signal that can be used to create images 34 of eye 12. An example of camera system 22 is a CCD camera. A sequence of images 34 of eye 12 ($i_1, \ldots, i_k, \ldots, i_n$) can show the movement of eye 12. An image 34 is used as a reference image to compare to a current image from camera 22 to detect movement. The reference image may any suitable image $i_{k-q}$, $q \geq 1$ before the current image $i_k$, e.g., the immediate previous image $i_{k-1}$ before the current image $i_k$.

Eye 12 has a location and orientation (or angular orientation or angular position), which may be described as the configuration of eye 12. In certain embodiments, the location of eye 12 may be expressed using (x, y, z) coordinates the coordinate system used in ophthalmological surgery, where an eye feature such as an iris defines an xy-plane, and the z-axis is the line normal to the plane an passing through a central point of eye 12. For example, the location of eye 12 on the xy-plane at time t may be given by (x(t), y(t)) coordinates of a central point of eye 12 (e.g., substantially about the pupil center or apex). The orientation, or angular position, of eye 12 may be expressed as rotation about a point of eye 12, which may be a central point of eye 12. For example, the orientation of eye 12 at time t may be given as an amount a(t) of degrees rotation away from a zero position at time t. The amount of degrees may be expressed with respect to one, two, or three axes, e.g.: a number $a_1(t)$ of degrees rotation about an axis $A_1$; a number $a_1(t)$ of degrees rotation about an axis $A_1$ and a number $a_2(t)$ of degrees rotation about an axis $A_2$; or a number $a_1(t)$ of degrees rotation about an axis $A_1$, a number $a_2(t)$ of degrees rotation about an axis $A_2$, and a number $a_3(t)$ of degrees rotation about an axis $A_3$. A zero position may be an initial angular position, such as the angular position of eye 12 when tracking starts at the beginning of a tracking session. A tracking session may start, e.g., at the initialization of tracking or at a restarting of tracking after, e.g., eye 12 has moved out of the tracking range.

Computer system 20 tracks the movement of eye 12 by determining a change in the configuration of eye 12, such as the translational and/or angular (or rotational) movement of eye 12. Translational movement is movement of all points of eye 12 by substantially the same amount in substantially the same direction. Angular movement is movement of points of eye 12 about a central point of eye 12. In certain embodiments, system 20 may use image processing to locate the central point of eye 12, e.g., the pupil, in the reference and current images 34 to determine translational movement and then translationally align the images 34 using the central point. System 20 may use image processing to locate features of eye 12 (e.g., blood vessels, iris features, or any other appropriate feature) to determine angular movement and then rotationally align the images 34 about the central point.

Figure 2A:
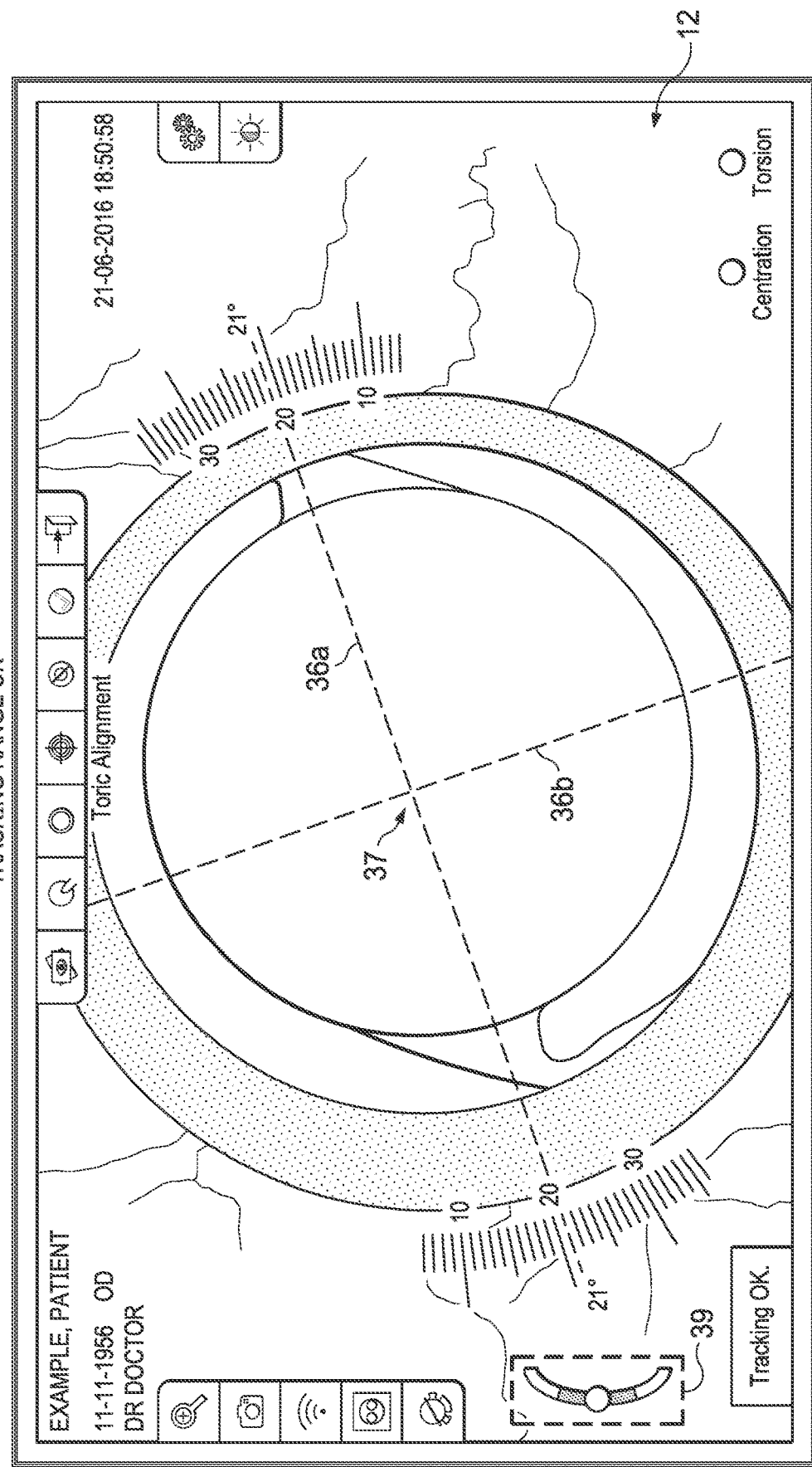
FIGS. 2A and 2B illustrate examples of range indicators during different tracking sessions.

FIG. 2A illustrates an example of showing the orientation (or angular position) of eye 12. One or more lines 36 may indicate the position of eye 12. In the illustrated example, lines 36*a*-*b* function as axes. Lines 36*a*-*b* pass substantially through a central point 37 of pupil of eye 12 and are substantially perpendicular to each other.

Referring back to FIG. 1, in some embodiments, system 10 tracks the movement of eye 12 to be able to align an overlay image of eye 12 over images 34 of eye 12 generated by camera system 22. Examples of an overlay image include a diagnostic image, an image of a treatment plan, an infrared image, or other image of eye 12. The overlay image may be placed over or blended with image 34 generated by camera system 22. When eye 12 moves in images 34, system 10 adjusts the overlay image to compensate for the movement.

Computer system 20 can track the movement of eye 12 within a certain tracking range where tracking can be properly performed, e.g., performed with suitable accuracy and/or precision. Outside of the range, system 10 system may suspend tracking or may report false positive tracking. The tracking range may be expressed as P+/−Q, where P represents a zero position when tracking starts and Q represents the tracking boundary, which is maximum distance away from the zero position P at which tracking can be properly performed. The tracking range may have one or more alert points. An alert point S is a point at which system 20 provides a notification eye 12 is close to or at the tracking boundary, so S≤Q.

For tracking angular movement, the tracking range may be expressed as P+/−Q°, where P represents zero rotation when tracking starts and Q represents the tracking boundary. The tracking boundary Q is the maximum amount of degrees away from the zero rotation P at which tracking can be properly performed. Q may have any suitable value. For current systems, Q is in the range of 10 to 15 degrees, such as 15 degrees. As systems improve, Q may be in the range of 15 to 20, 20 to 25, 25 to 30 or greater than 30 degrees. Alert point S may have any suitable value, and may be selected based on Q. For example, S=Q or S=Q−T, where T in the range of 1 to 5, 5 to 10, 10 to 15, 15 to 20 or greater than 20 degrees, such as S=Q−T=15−5 degrees. Alert point S may be set by system 10, or may be set by user through user input.

As computer system 20 tracks the movement of eye 12, system 20 also determines the configuration of eye 12 relative to an alert point. For example, system 20 determines the orientation a(t) of eye 12 relative to an alert point S. The relationship may be expressed as a difference between the orientation of eye 12 and the alert point, e.g., a(t)−S. As eye 12 moves closer to the alert point S, the difference approaches zero.

Output device 26 outputs a range indicator that indicates the configuration (e.g., orientation and/or location) of eye 12 relative to the alert point S of the tracking range. Output device 26 may be any suitable device that provides computer output to a user or another computer, e.g., a display, monitor, projector, speaker, headphone, or printer. In certain embodiments, output device 26 is a display that shows the range indicator as a graphical element. A graphical element is a visual mark of any suitable size, shape, or color that typically conveys information. Examples of graphical element range indicators are described with reference to FIGS. 2A to 9B. In certain embodiments, output device 26 is a speaker that emits the range indicator as a sound. Examples of audio range indicators are described with reference to FIGS. 10A to 11B.

Figure 2B:
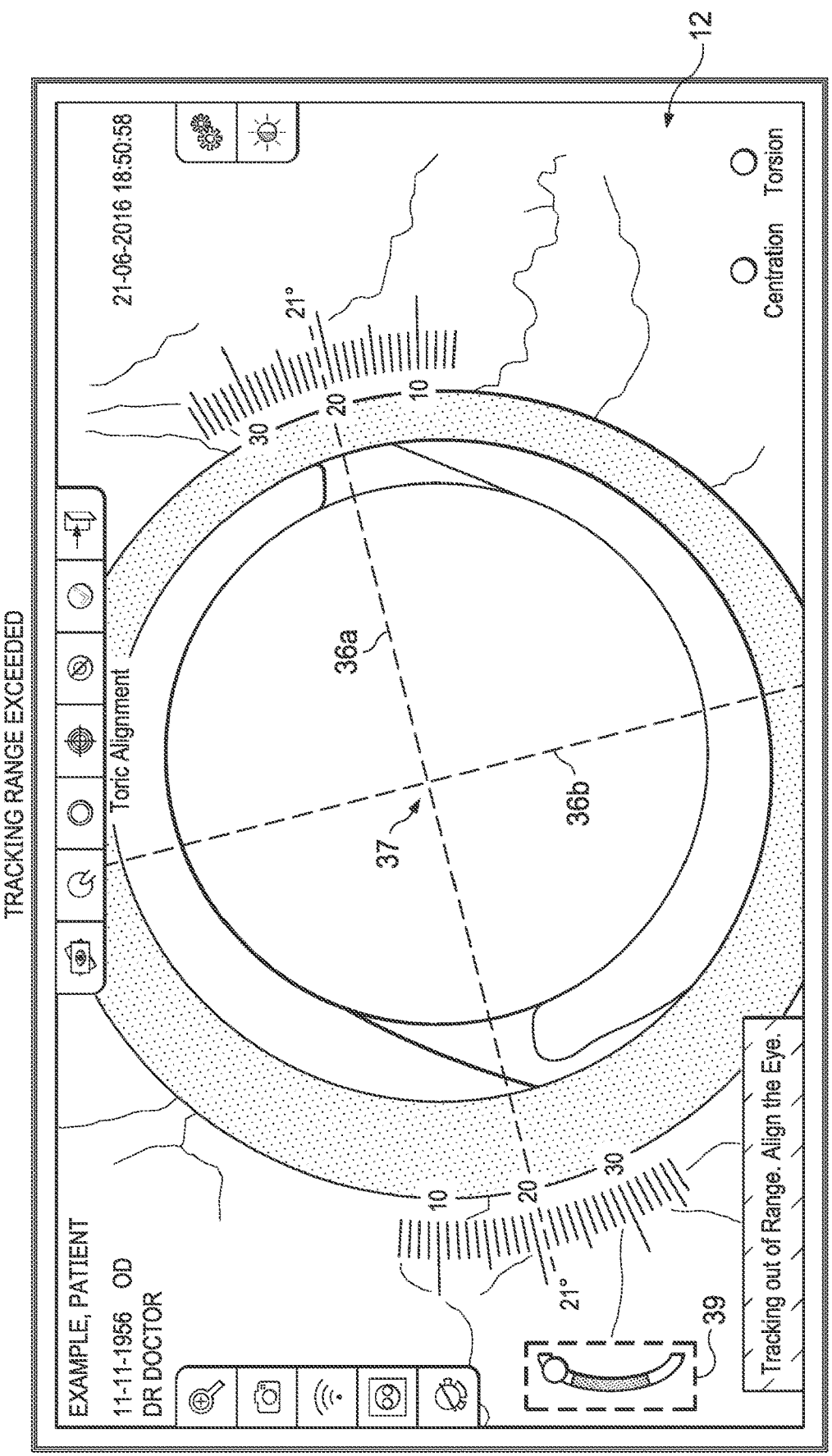

Referring to FIGS. 2A and 2B, range indicator 39 indicates the orientation of eye 12 during different tracking sessions. In FIG. 2A, the zero point of the tracking session is $P_1$, so the tracking range of the session is $P_1$+/−Q. In FIG. 2B, the zero point of the tracking session is $P_2$, so the tracking range of the session is $P_2$+/−Q. In FIG. 2A, range indicator 39 indicates the orientation of eye 12 is within the tracking range. In FIG. 2B, range indicator 39 indicates the orientation of eye 12 is outside of the tracking range. Note the orientation of eye 12 appears to be the same in both FIGS. 2A and 2B, even though eye 12 of FIG. 2A is within the tracking range and eye 12 of FIG. 2B is not. This is because FIGS. 2A and 2B describe different tracking sessions, and the determination of whether eye 12 is within the tracking range P+/−Q depends on the zero point P of the tracking session.

Referring back to FIG. 1, laser system 24 receives a notification of the movement of eye 12, and changes a laser beam position in response to the notification. Laser system 24 may be any suitable laser surgical device that provides a laser beam to treat eye 12, and may comprise a computer, laser source, and scanning device. In certain embodiments, the scanning device receives the notification of the movement of eye 12 and modifies the focus of the laser beam to address or compensate for the movement. In this manner, eye movements can be taken into account either for registration or for tracking purposes.

Figures 3A, 3B, 4A, 4B:
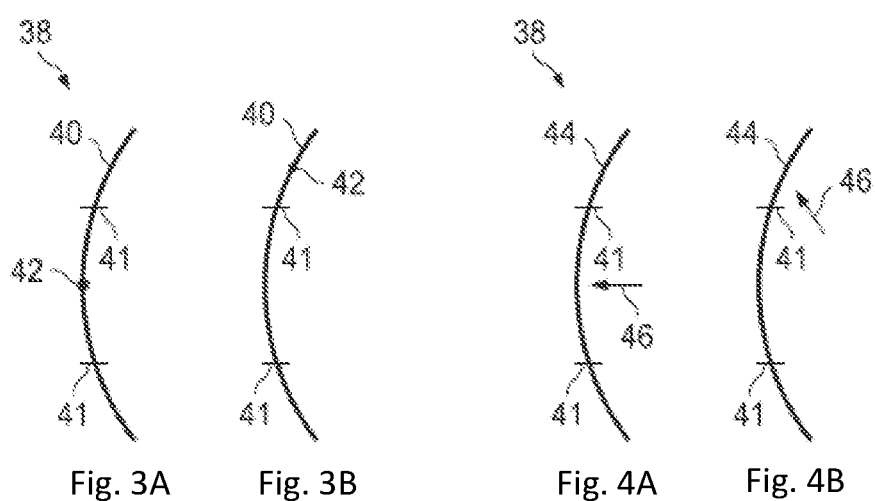
FIGS. 3A and 3B illustrate an example of a graphical element with a slider element.
FIGS. 4A and 4B illustrate an example of a graphical element with an arrow element.

FIGS. 3A and 3B illustrate an example of a graphical element 38 with a slider element 42. In the example, graphical element 38 includes a linear element 40 and a slider element 42. Linear element 40 is a long, narrow mark that can be straight or curved. In the example, linear element 40 represents the tracking range and has at least one alert point element 41 representing an alert point of the tracking range. Slider element 42 is a mark along linear element 40. In the example, slider element 42 represents the rotation of eye 12. The position of the slider element 42 relative to point 41 represents the rotation of eye 12 relative to the alert point of the tracking range. FIG. 3A shows the rotation of eye 12 not exceeding an alert point, i.e., is within an acceptable range. FIG. 3B shows the rotation eye 12 exceeding an alert point, i.e., is outside of an acceptable range.

FIGS. 4A and 4B illustrate an example of a graphical element 38 with an arrow element 46. In the example, graphical element 38 includes a linear element 44 and an arrow element 46. Linear element 44 is similar to linear element 40. In the example, linear element 44 represents the tracking range and has at least one alert point element 41 representing an alert point of the tracking range. Arrow element 46 is a mark that indicates a position along linear element 44. In some cases, arrow element 46 may look like as illustrated or may look like a compass needle. In the example, arrow element 46 points to a point of linear element 44 that represents the rotation of eye 12. The position where arrow element 46 points relative to point 41 represents the rotation of eye 12 relative to the alert point of the tracking range. FIG. 4A shows the rotation of eye 12 not exceeding an alert point, i.e., is within an acceptable range. FIG. 4B shows the rotation eye 12 exceeding an alert point, i.e., is outside of an acceptable range.

FIGS. 5A to 5D illustrate an example of a graphical element 38 that changes color. In certain embodiments, graphical element 38 changes continuously from a first color to a second color to indicate a change in the orientation of the eye relative to an alert point of the tracking range. The continuous color change may be changes in shade from the first color to the second color. In the illustrated example, FIG. 5A shows a green graphical element 38, indicating the rotation of eye 12 is not close to an alert point, i.e., is within an acceptable range. FIG. 5B shows a reddish green graphical element 38, indicating the rotation of eye 12 is approaching the alert point. FIG. 5C shows a greenish red graphical element 38, indicating the rotation of eye 12 is even closer to the alert point. FIG. 5D shows a red graphical element 38, indicating the rotation of eye 12 has exceeded the alert point, i.e., is outside of the acceptable range.

FIGS. 6A to 6D illustrate an example of a graphical element 38 that changes shape. In certain embodiments, graphical element 38 changes continuously from a first shape to a second shape to indicate a change in the orientation of the eye relative to an alert point of the tracking range. The continuous change in shape may be gradual changes from the first shape to the second shape. In the illustrated example, FIG. 6A shows graphical element 38 as a circle, indicating the rotation of eye 12 is not close to an alert point, i.e., is within an acceptable range. FIG. 6B shows graphical element 38 as a square with rounded corners, indicating the rotation of eye 12 is approaching the alert point. FIG. 6C shows graphical element 38 as an X with rounded corners, indicating the rotation of eye 12 is even closer to the alert point. FIG. 6D shows graphical element 38 as an X with sharp corners, indicating the rotation of eye 12 has exceeded the alert point, i.e., is outside of the acceptable range.

FIGS. 7A and 7B illustrate an example of a graphical element 38 that changes size. In certain embodiments, graphical element 38 changes continuously from a first size to a second size to indicate a change in the orientation of the eye relative to an alert point of the tracking range. An alert point mark 47 represents the alert point. In the illustrated example, FIG. 7A shows graphical element 38 as a bar that does not cross mark 47, indicating the rotation of eye 12 does not exceed an alert point, i.e., is within an acceptable range. FIG. 7B shows graphical element 38 as a bar that crosses mark 47, indicating the rotation of eye 12 exceeds an alert point, i.e., is outside of an acceptable range.

FIGS. 8A to 8D illustrate an example of a graphical element 38 that displays numbers. In certain embodiments, graphical element 38 displays a first number 50 that continuously changes to subsequent numbers 50 to indicate a change in the orientation of the eye relative to an alert point of the tracking range. In the illustrated example, FIG. 8A shows graphical element 38 displaying "3", indicating the rotation of eye 12 is not close to an alert point, i.e., is within an acceptable range. FIG. 8B shows graphical element 38 displaying "2", indicating the rotation of eye 12 is approaching the alert point. FIG. 8C shows graphical element 38 displaying "1", indicating the rotation of eye 12 is even closer to the alert point. FIG. 8D shows graphical element 38 displaying "0", indicating the rotation of eye 12 has exceeded the alert point, i.e., is outside of the acceptable range.

FIGS. 9A to 9D illustrate an example of a graphical element 38 that displays words. In certain embodiments, graphical element 38 displays a first word 52 that continuously changes to subsequent words 52 to indicate a change in the orientation of the eye relative to an alert point of the tracking range. In the illustrated example, FIG. 9A shows graphical element 38 displaying "OK", indicating the rotation of eye 12 is not close to an alert point, i.e., is within an acceptable range. FIG. 9B shows graphical element 38 displaying "CLOSE", indicating the rotation of eye 12 is approaching the alert point. FIG. 9C shows graphical element 38 displaying "TOO CLOSE", indicating the rotation of eye 12 is even closer to the alert point. FIG. 9D shows graphical element 38 displaying "NO", indicating the rotation of eye 12 has exceeded the alert point, i.e., is outside of the acceptable range.

FIGS. 10A and 10B illustrate an example of a sound that changes in frequency. In certain embodiments, a speaker 56 emits a sound that continuously changes in frequency 58 to indicate a change in the orientation of the eye relative to an alert point of the tracking range. In the example, FIG. 10A shows a sound with a frequency 58a of x Hz indicating the rotation of eye 12 is not close to an alert point, i.e., is within an acceptable range. FIG. 10B shows a sound with a frequency 58b of y Hz indicating the rotation of eye 12 exceeds an alert point, i.e., is outside of an acceptable range. Frequency y can be greater or less than frequency x, but not the same as frequency x.

FIGS. 11A and 11B illustrate an example of a sound that changes in volume 60. In certain embodiments, a speaker 56 emits a sound that continuously changes in volume 60 to indicate a change in the orientation of the eye relative to an alert point of the tracking range. In the example, FIG. 11A shows a sound with a volume 60a of x dB indicating the rotation of eye 12 is not close to an alert point, i.e., is within an acceptable range. FIG. 11B shows a sound with a volume 60*b* of y dB indicating the rotation of eye 12 exceeds an alert point, i.e., is outside of an acceptable range. Volume y can be greater or less than volume x, but not the same as volume x.

In certain cases, a speaker 56 emits words to indicate a change in the orientation of the eye relative to an alert point of the tracking range. Any suitable words may be used, e.g., the words described relative to FIGS. 9A and 9B. Other examples of words include "rotate clockwise" if the tracking should be rotated clockwise to avoid exceeding the tracking range, or "rotate counter-clockwise" if the tracking should be rotated counter-clockwise to avoid exceeding the tracking range.

FIG. 12 illustrates an example of a method for tracking the movement of an eye that may be performed by system 10 of FIG. 1. In the example, the method starts at step 110, where images of the eye are generated. At step 112, the images are stored, and at least one image is stored as a reference image. Steps 114 and 116 describe tracking eye 12 within a tracking range with one or more alert points. Eye 12 is tracked at step 114 by comparing a current image of the plurality of images with the reference image. Movement of eye 12 is determined from the comparison of the current image and the reference image at step 116. The orientation of the eye is determined relative to an alert point of the tracking range at step 118. A range indicator that indicates the orientation of the eye relative to the alert point of the tracking range is output at step 120.

A component (e.g., a computer) of the systems and apparatuses disclosed herein may include an interface, logic, and/or memory, any of which may include hardware and/or software. An interface can receive input to the component, provide output from the component, and/or process the input and/or output. Logic can perform the operations of the component, e.g., execute instructions to generate output from input. Logic may be a processor, such as one or more computers or one or more microprocessors. Logic may be computer-executable instructions encoded in memory that can be executed by a computer, such as a computer program or software. A memory can store information and may comprise one or more tangible, non-transitory, computer-readable, computer-executable storage media. Examples of memory include computer memory (e.g., Random Access Memory (RAM) or Read Only Memory (ROM)), mass storage media (e.g., a hard disk), removable storage media (e.g., a Compact Disk (CD) or a Digital Video Disk (DVD)), and network storage (e.g., a server or database).

Although this disclosure has been described in terms of certain embodiments, modifications (such as substitutions, additions, alterations, or omissions) of the embodiments will be apparent to those skilled in the art. Accordingly, modifications may be made to the embodiments without departing from the scope of the invention. For example, modifications may be made to the systems and apparatuses disclosed herein. The components of the systems and apparatuses may be integrated or separated, and the operations of the systems and apparatuses may be performed by more, fewer, or other components. As another example, modifications may be made to the methods disclosed herein. The methods may include more, fewer, or other steps, and the steps may be performed in any suitable order.

What is claimed is:

1. A system for tracking movement of an eye, comprising:
a camera system configured to generate a plurality of images of the eye;
a computer system comprising:
a memory configured to store the plurality of images and store at least one of the images as a reference image; and
one or more processors configured to:
track movement of the eye within a tracking range by comparing a current image of the plurality of images with the reference image, and by determining a rotational movement of the eye from the comparison of the current image and the reference image, the tracking range having a plurality of alert points comprising a tracking boundary point and an intermediate point, the tracking boundary point representing a maximum number of degrees away from a zero point where tracking can be properly performed, the intermediate point located between the zero point and the tracking boundary point; and
determine an orientation of the eye relative to at least one alert point of the tracking range; and
an output device configured to output a range indicator that indicates the orientation of the eye relative to the at least one alert point of the tracking range, the output device comprising a speaker that outputs the range indicator as:
a first sound if the orientation of the eye corresponds to a point between the intermediate point and the tracking boundary point indicating the eye is nearing a tracking boundary beyond which tracking cannot be performed; and
a second sound different from the first sound if the orientation of the eye corresponds to a point beyond the tracking boundary point where tracking cannot be performed.

2. The system of claim 1, wherein the output device comprises a display that shows the range indicator as a graphical element.

3. The system of claim 2, wherein the graphical element comprises:
a linear element representing the tracking range, the linear element having at least one alert point element representing the at least one alert point of the tracking range; and
a slider element corresponding to the eye, the position of the slider relative to the alert point element representing the orientation of the eye relative to the at least one alert point of the tracking range.

4. The system of claim 2, wherein the graphical element comprises:
a linear element representing the tracking range, the linear element having at least one alert point element representing the at least one alert point of the tracking range; and
an arrow element corresponding to the eye, the position where the arrow points relative to the alert point element representing the orientation of the eye relative to the at least one alert point of the tracking range.

5. The system of claim 2, wherein the graphical element changes continuously from a first color to a second color to indicate a change in the orientation of the eye relative to the at least one alert point of the tracking range.

6. The system of claim 2, wherein the graphical element changes continuously from a first shape to a second shape to indicate a change in the orientation of the eye relative to the at least one alert point of the tracking range.

7. The system of claim 2, wherein the graphical element changes continuously from a first size to a second size to indicate a change in the orientation of the eye relative to the at least one alert point of the tracking range.

8. The system of claim 2, wherein the graphical element shows a first number that continuously changes to a second number to indicate a change in the orientation of the eye relative to the at least one alert point of the tracking range.

9. The system of claim 2, wherein the graphical element shows a first word that changes to a second word to indicate a change in the orientation of the eye relative to the at least one alert point of the tracking range.

10. The system of claim 1, wherein the speaker emits a sound that continuously changes in frequency to indicate a change in the orientation of the eye relative to the at least one alert point of the tracking range.

11. The system of claim 1, wherein the speaker emits a sound that continuously changes in volume to indicate a change in the orientation of the eye relative to the at least one alert point of the tracking range.

12. The system of claim 1, wherein the speaker emits words to indicate a change in the orientation of the eye relative to the at least one alert point of the tracking range.

13. The system of claim 1, wherein the image processing system receives a selection of an alert point of the one or more alert points from user input.

14. The system of claim 1, further comprising a laser system configured to:
   receive a notification of the movement of the eye; and
   change a laser beam position in response to the notification.

15. The system of claim 1, wherein:
   the tracking boundary point is in a range of 10 to 15 degrees.

16. The system of claim 1, wherein:
   the intermediate point is one to ten degrees away from the tracking boundary point.

17. The system of claim 1, wherein:
   the intermediate point is set by the system.

18. The system of claim 1, wherein:
   the intermediate point is set in response to user input.

19. A method for tracking the movement of an eye, comprising:
   generating a plurality of images of the eye;
   storing the plurality of images and at least one of the images as a reference image; and
   tracking movement of the eye within a tracking range by comparing a current image of the plurality of images with the reference image, and by determining a rotational movement of the eye from the comparison of the current image and the reference image, the tracking range having a plurality of alert points comprising a tracking boundary point and an intermediate point, the tracking boundary point representing a maximum number of degrees away from a zero point where tracking can be properly performed, the intermediate point located between the zero point and the tracking boundary point and determining an orientation of the eye relative to at least one alert point of the tracking range; and
   outputting a range indicator that indicates the orientation of the eye relative to the at least one alert point of the tracking range, the output device comprising a speaker that outputs the range indicator as:
      a first sound if the orientation of the eye corresponds to a point between the intermediate point and the tracking boundary point indicating the eye is nearing a tracking boundary beyond which tracking cannot be performed; and
      a second sound different from the first sound if the orientation of the eye corresponds to a point beyond the tracking boundary point where tracking cannot be performed.

* * * * *